United States Patent
Richter (10) Patent No.: US 8,354,849 B2
(45) Date of Patent: Jan. 15, 2013

(54) METHOD AND DEVICE FOR HUMIDITY AND/OR DENSITY MEASUREMENT

(75) Inventor: Hendrik Richter, Hamburg (DE)

(73) Assignee: TEWS Elektronik GmbH & Co. KG, Hamburg (DE)

( * ) Notice: Subject to any disclaimer, the term of this patent is extended or adjusted under 35 U.S.C. 154(b) by 252 days.

(21) Appl. No.: 12/740,724

(22) PCT Filed: Nov. 19, 2008

(86) PCT No.: PCT/EP2008/009775
§ 371 (c)(1), (2), (4) Date: Aug. 9, 2010

(87) PCT Pub. No.: WO2009/065568
PCT Pub. Date: May 28, 2009

(65) Prior Publication Data
US 2010/0295556 A1   Nov. 25, 2010

(30) Foreign Application Priority Data
Nov. 20, 2007   (DE) .......................... 10 2007 057 092

(51) Int. Cl.
G01N 22/04 (2006.01)
(52) U.S. Cl. ........................................ 324/640; 324/643
(58) Field of Classification Search .................. 324/640, 324/639, 637, 629, 600, 634, 643, 664, 689, 324/694
See application file for complete search history.

(56) References Cited

U.S. PATENT DOCUMENTS

| | | |
|---|---|---|
| 3,079,551 A | 2/1963 | Walker |
| 3,501,692 A | 3/1970 | Kluck |
| 3,681,684 A | 8/1972 | Busker et al. |
| 4,132,943 A * | 1/1979 | Gournay et al. .............. 324/335 |
| 4,319,185 A | 3/1982 | Hill |

(Continued)

FOREIGN PATENT DOCUMENTS

DE   2928847   3/1984

(Continued)

OTHER PUBLICATIONS

"Non-Contacting Determination of Moisrure Content in Bulk Materials Using Sub-Nanosecond UWB-Pulses", by O' Schimmer, 34th European Microwave Conference, Amsterdam, 2004, pp. 677-680.

(Continued)

*Primary Examiner* — Hoai-An D Nguyen
(74) *Attorney, Agent, or Firm* — Vidas, Arrett & Steinkraus, P.A.

(57) ABSTRACT

A method for the measurement of humidity and/or density in a measurement target. The phase and the amplitude of the microwave radiation transmitted through the measurement target is determined for a number of frequencies. The complex-valued transmission function of the measurement target is calculated from the determined values using the complex-valued transfer function of the measurement arrangement, and transformed into the time domain as a complex-valued time domain function. The point in time at which the amount of the main pulse has its maximum value is determined as a characteristic variable A from the time domain function. From the time domain function, the width of the main pulse is determined as a characteristic variable B, and/or the amplitude value of the main pulse as a characteristic variable H. A humidity and/or density of the measurement target is determined depending on the characteristic variable A and the characteristic variables B and/or H.

28 Claims, 3 Drawing Sheets

U.S. PATENT DOCUMENTS

| | | | |
|---|---|---|---|
| 4,727,311 | A | 2/1988 | Walker |
| 4,788,853 | A | 12/1988 | Bell |
| 5,333,493 | A | 8/1994 | Cutmore |
| 5,939,888 | A * | 8/1999 | Nelson .................... 324/640 |
| 6,025,724 | A | 2/2000 | Moshe et al. |
| 2004/0002338 | A1 | 1/2004 | Spartz et al. |
| 2004/0239338 | A1 | 12/2004 | Jonsson et al. |
| 2005/0253595 | A1 | 11/2005 | France |

FOREIGN PATENT DOCUMENTS

| | | |
|---|---|---|
| DE | 40 04 119 C2 | 9/1993 |
| DE | 4208863 | 9/1993 |
| DE | 202007001196 | 3/2011 |
| EP | 0 935 136 A2 | 8/1999 |
| WO | 00/09983 | 2/2000 |

OTHER PUBLICATIONS

"Estimation of Electromagnetic of Libyan soil Properties by Stepped Frequency Radar" by S. I. Elkhetali, Copyright 2007, pp. 110-113.

"Modeling of Ground-Penetrating Radar for Accurate Characterization of Subsurface Electric Properties" by Sebastien Lambot et al, Transaction Geoscience and Remot Sensing, vol. 42, No. 11, Nov. 2004, pp. 2555-2568.

"Frequency Dependence of the Soil Electromagnetic Properties Derived from Ground-Penetrating Radar Signal Inversion" by Sebastien Lambot et al, Subsurface Sensing Technologies and Applications, vol. 6, No. I, Jan. 2005, pp. 73-87.

"Dielectric Permittivity and Scattering Measurements of Greenland Firn at 26.5-40 GHz", by V. I. Lytle et al, IBEE Transactions on Geoscience adn Remote Sensing, vol. 32, No. 2, Mar. 1994, pp. 290-295.

Nyfors; Vainikainen, Industrial Measurement Sensors, International Standard Book No. 0-89006-397-4. Library of congress Catalog Card No. 89-15197.

Sachs, Principles of Ultra-Wideband Sensor Electronics, Library of congress Control No. 20044109775, Part of Springer Science and Business Media; Springer-Verlag Berlin Heidelberg 2005, Printed in Germanyu.

* cited by examiner

METHOD AND DEVICE FOR HUMIDITY AND/OR DENSITY MEASUREMENT

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to a method and an apparatus for the measurement of humidity and/or density on a measurement target using the microwave technique. The present invention is particularly related to non-contact measurement of a humidity value that is independent of the density and the thickness of the measurement target, and/or or a humidity-independent value of the density by surface, which can be converted into a density when the thickness is known. On dielectric materials, the measurement takes place by the transmission of electromagnetic radiation through the measurement target. The present invention can be applied to all kinds of measurement targets, in particular in the humidity measurement of big bales and cardboard boxes, filled for instance with tea, tobacco, cotton, textiles, pulps, organic materials and the like, and also for board-shaped measurement targets like for instance wood boards, press boards, MDF boards, building materials, gypsum, polystyrene foam, plastic materials and the like. The present invention is further suited for use with stationary or moving goods, like for instance grain, cereals, dried fruits and vegetables, granulates and the like.

From DE 40 04 119 C2, it is for instance known that humidity measurement with electromagnetic waves is possible on dielectric materials. Such a measurement is based on the fact that water has a great complex refraction coefficient n-ik, so that the dielectric properties of the humid measurement target are decisively determined by the dielectric properties of the water contained therein. Besides to the fact that water has a great complex refraction coefficient, it is important for the analysis of the measurement that the complex refraction coefficient is proportional to the density of the measurement target. Electromagnetic waves that interact with the measurement target experience attenuation in the measurement target, as well as a wavelength shortening. The attenuation of the electromagnetic waves is the greater the higher the material's reactive component k of the complex refraction coefficient is. The wavelength shortening of the electromagnetic wave is the more marked the higher the material's active component n of the complex refraction coefficient is. Therefore, both effects are the higher the greater the humidity and density of the material are.

The measurement of the complex refraction index of a measurement target is particularly successful with microwave resonators, compare DE 40 04 119 C2 e.g. Here, the change of the resonance width and the shift of the resonance frequency of the filled resonator with respect to the unfilled resonator are acquired, and by doing so, characteristic variables are determined for the reactive component and the active component of the complex refraction index or the complex dielectric constant, respectively, of the measurement target. Then, using further specific parameters, a density-independent humidity value and/or a humidity-independent density value are determined for the measurement target. Because the electromagnetic field is bound to the resonator and penetrates into the measurement target only up to a small depth of about half a wavelength, at spacious measurement targets and in particular when leakage sensors are used, resonator methods are in principle subject to the technical limitation to be able to capture humidity and density only at the surface, but not in the core of the measurement target. Moreover, the resonator must always be brought into direct proximity of the measurement target, mostly even be in contact with the same.

The detection of humidity and/or density in the core of spacious measurement targets, like for instance in big cardboard boxes or bales, is necessary in many applications. Transmission measurements are used in microwave technique for this, wherein microwave radiation is radiated through the measurement target.

From U.S. Pat. No. 4,727,311, a transmission measurement method is known in which the humidity content in the measurement target is determined using microwaves. For this purpose, two microwave input signals having different frequencies are used, and their respective attenuations are measured. The humidity is determined from the attenuation. In order to determine the density of the measurement target, the phase shift of the microwave signals in the measurement target is acquired.

From U.S. Pat. No. 5,333,493, an apparatus and a method is known for determining the humidity content in a sample which is transported through a measurement arrangement on a conveyor belt. A series of microwave signals having discrete frequencies is used for measurement. The phase shift of the received signals is averaged, and is analysed together with a weight of the measurement target determined by weighing, in order to determine the humidity.

From U.S. Pat. No. 6,025,724, an apparatus and a method is known for determining the humidity content in packaged goods. The phase shift and the attenuation of the received microwaves are measured plural times in this, the microwaves permeating the measurement target in different regions. Adding a further characteristic variable for the measurement target, a rough value for a corrected attenuation is determined from the measured values for the attenuation, which then serves to determine the humidity.

From US 2004/0239338 A1, a method and an apparatus for measuring the humidity and/or the salt content in a measurement target are known. Polarized microwave radiation is radiated through the measurement target in this, and the reflected radiation is analysed. The humidity is then determined from the attenuation of the reflected radiation.

From US 2005/0253595 A1, an apparatus and a method is known for determining the humidity, wherein the phase shift and the attenuation of the transmitted radiation are analysed. Further, the thickness of the sample is measured separately in order to analyse the humidity of the sample.

From an article by O. Schimmer et al., "Noncontacting determination of moisture content in bulk materials using sub-nanosecond UWB-pulses", Microwave Theory and Techniques, IEEE Transactions, June 2005, a method is known in which a short quasi-Gaussian pulse of electromagnetic waves is generated and emitted via a sending antenna, which then penetrates through the measurement target and is received again by a receiving antenna. With the aid of multivariate calibration, of principal component regression (PCR) or of an artificial neuronal network, the shape of the transmitted pulse is compared with the shape of the transmitted pulse without measurement target. With this technique, at least two measurement variables can be obtained which can be used for density-independent humidity measurement.

From U.S. Pat. No. 4,319,185, a method is known in which an electromagnetic pulse is emitted whose height after transmission through the measurement target is used as a characteristic variable for the humidity. In this method, solely the attenuation is acquired, so that an additional density measurement is necessary to determine a density-independent humidity value.

BRIEF SUMMARY OF THE INVENTION

The present invention is based on the objective to provide a method and an apparatus for the measurement of humidity and/or density in a measurement target, wherein accurate values for humidity and/or density can be determined by means that are as simple as possible, and for very different measurement targets in different spatial positions with respect to the measurement arrangement.

The method of the present invention serves for the measurement of humidity and/or density in a measurement target by means of a microwave sender and a microwave receiver. Further provided is an analysing unit, which can determine the phase and the amplitude for radiation of the microwave sender received by the microwave receiver, and in which a complex-valued transfer function of the measurement arrangement can be memorised. The complex-valued transfer function of the measurement arrangement indicates how an electromagnetic wave changes in its phase and its amplitude depending on the frequency when it passes through the measurement arrangement in the case that there is no measurement target between microwave sender and microwave receiver. In the method of the present invention, the phase and the amplitude of the microwave radiation transmitted through the measurement target is determined for a number of frequencies in one measurement operation, the values form the complex-valued transfer function of the measurement target. Using the complex-valued transfer function of the measurement arrangement, the complex-valued transmission function of the measurement target is calculated from the determined values. The transmission function of the measurement target is a transfer function for the measurement target which describes how the electromagnetic wave changes in its phase and its amplitude when it passes through the measurement target. The complex-valued transmission function of the measurement target is transformed into the time domain, into a complex-valued time domain function. From the time domain function, that point of time at which the main pulse has its maximum value is determined as a characteristic variable A. Further, the width of the main pulse of the complex-valued time domain function, preferably its half-band width, is determined as a characteristic variable B, and/or the amplitude value of the main pulse as a characteristic variable H from the time domain function. The humidity and/or the density of the measurement target are determined from the characteristic variable A and the characteristic variables B and/or H. That pulse in the time domain is regarded as the main pulse which has the greatest amplitude value and/or the greatest energy.

In contrast to known transmission measurement methods, the method of the present invention works with a representation of the measurement signals in the frequency domain as well as in the time domain in the analysis of the measurement signals. Frequency domain representations and time domain representations are complementary representations of functions that can be converted into each other by the Fourier transform. The method of the present invention works at first in the frequency domain, where the complex-valued transmission function of the measurement target is calculated using the transfer function of the measurement arrangement and the transfer function of the measurement target which is acquired for a series of preferably discrete frequencies. In doing so it is taken advantage of the fact that in the measurement of the microwave radiation transmitted through the measurement target in the measurement arrangement, the change of the amplitude and the phase can be represented in the frequency domain as a product of the transfer function in the measurement arrangement and of the transmission function of the measurement target. The transmission function of the measurement target describes the alteration of the electromagnetic radiation by the measurement target, wherein the influences by the measurement arrangement, like for instance emission characteristics and reception characteristics of microwave sender and microwave receiver, respectively, are already subtracted out. However, the transmission function of the measurement target obtained in this way still includes the influences of microwave radiation that was reflected on boundary surfaces of the measurement target and has interfered with the transmitted or impingent radiation. In order to exclude these influences, the complex-valued transmission function of the measurement target is transformed into the time domain function according to the present invention. In the time domain function, the signals arisen by reflection are no longer superimposed to the intrinsic measurement signal, but due to their greater runtime between microwave sender and microwave receiver, they occur later in the time domain function than the intrinsic measurement signal. By utilising the main pulse of the time domain function in the analysis of the time domain function, disturbing influences on the measurement signal are suppressed. The occurrence of the main pulse of the time domain function yields a very reliable starting value for a later analysis of the measurement signals, which subsequently results a in humidity and/or density value for the measurement target. The measurement signals are then analysed in a per se known way, for instance by analysing the characteristic variable A for the runtime delay of the signal by the measurement target, and the characteristic variable B for the width of the main pulse or the characteristic variable H for the amplitude value of the main pulse. In this, the characteristic variable B as well as the characteristic variable H are a measure for the reactive component of the complex refraction coefficient and the thickness of the measurement target, whereas the characteristic variable A can be analysed as a measure for the active component of the complex refraction coefficient and the thickness of the measurement target. From the characteristic variable A and at least one further characteristic variable B or H, the humidity of the measurement target is determined independently of the density, and/or the density of the measurement target is determined independently of the humidity. A particular advantage of the method of the present invention is that the obtained characteristic variables are independent of the exact position or the exact alignment of the measurement target in the measurement arrangement between microwave sender and microwave receiver. A further particular advantage of the method of the present invention is that the humidity measured in this way is also independent of the thickness of the measurement target.

In a preferred embodiment of the method of the present invention, in a measurement operation without measurement target between microwave sender and microwave receiver, the phase and the amplitude of the microwave radiation emitted by the microwave sender is determined for a number of frequencies, and the complex-valued transfer function of the measurement arrangement is determined from this and saved in the analysing unit. In this measurement operation, it can be determined for one or plural subsequent measurements with measurement target which transfer properties the pure measurement arrangement has. Possible changes of the measurement arrangement, which had been occurred for instance by changes of the surroundings conditions or by shocks against sender or receiver before the measurement of the transfer function of the measurement arrangement, can be compensated in this way and do not have any influence on the measurement results.

There are different approaches to analyse the complex-valued time domain function, in particular to determine the point of time in which the amount of the main pulse has its maximum value. In a preferred embodiment of the present invention, the amount of the complex time domain function is analysed. Alternatively, it is also possible to use the active component and/or the reactive component of the complex time domain function in the determination of the characteristic variables.

In a practical extension of the method of the present invention, the frequencies are selected in the measurement operation from out a frequency interval having a lowest frequency $f_{Start}$ and a highest frequency $f_{Stop}$. A preferred frequency interval is 500 kHz to 50 GHz. In the determination of the transfer function of the measurement arrangement as well as in that of the transfer function of the measurement target, it is preferably worked with frequencies of the same frequency interval.

In a particularly preferred embodiment of the method of the present invention, the characteristic variable B is calculated depending on the amplitude value H, taking into account the lower frequency $f_{Start}$ and the upper frequency $f_{Stop}$ of the frequency interval. As the measurement operation is always performed for a finite frequency interval, the frequency interval of the transmission function has purposefully to be taken into account in the analyses in the time domain. In order to avoid an influence of the frequency interval limitation on the characteristic variables B and H, the variables B and H are set in a relation to each other, and by doing so the characteristic variable B is preferably determined from the characteristic variable H, taking into account the finite frequency interval. Alternatively, it is also possible to determine the characteristic variable H from the characteristic variable B, taking into account the finite frequency interval.

In a preferred extension of the method of the present invention, the characteristic variable B is determined as the reciprocal value of the amplitude value H.

For the humidity of the measurement target, a humidity value $\phi$ is determined that depends on at least two characteristic variables. Preferably, the humidity value $\phi$ is specified as a density-independent value, by defining it depending on the quotient of the characteristic variables B and A. Alternatively, the humidity value $\phi$ may also be limited in the range of its values by using the arc tan function in its value range.

By the method of the present invention, even the density by surface or the density, respectively, of the measurement target can be determined besides to the humidity, depending on the humidity value $\phi$ and the characteristic variables A and B. The density by surface depends preferably on the product of the humidity value and the characteristic variable B, wherein a constant can be purposefully added to the humidity value $\phi$ before the multiplication with the characteristic variable A.

In a further, preferred embodiment, the active component and the reactive component of the complex refractive index of the measurement target can be determined from the characteristic variables A and B. Preferably, the active component of the measurement target reduced by 1 is obtained by dividing the characteristic variable A through the spatial extension of the measurement target in the propagation direction of the microwave, and the reactive component of the measurement target by dividing the characteristic variable B through the spatial extension of the measurement target in the propagation direction of the microwave.

In a further, preferred embodiment, a density by surface d of the measurement target can be determined depending on the humidity value $\phi$ and the characteristic variables A or B. An average humidity value d is preferably obtained by dividing the density by surface d through the spatial extension of the measurement target in the propagation direction of the microwave.

In a preferred extension of the method of the present invention, the determination of humidity, density by surface and/or density takes place depending on at least one measured temperature. The measured temperatures may be a temperature of the measurement target, a temperature of the measurement arrangement and/or a temperature of the surroundings. The acquisition of the temperature permits to analyse the measured characteristic variables depending on temperature, wherein an analysis may even take place with plural measured temperature values. The result of the analysis is then independent of the temperature.

In a preferred embodiment of the measurement method of the present invention, the microwave sender emits polarized microwave radiation. In a possible embodiment, circularly polarized microwave radiation is emitted.

In an alternative embodiment, linearly polarized microwave radiation is emitted by the microwave sender, wherein the measurement operation is repeated plural times for each measurement target with different polarization directions. The polarization direction is changed with respect to the already used polarization direction in every repetition. An analysis of the measurement operation with different polarization angles is performed such that the analysis takes place for that polarization angle at which the characteristic variable B takes on a minimum value.

In a preferred embodiment, the measurement target is moved between microwave sender and microwave receiver, in particular, the movement takes place during the measurement operation and transversally to the propagation direction of the microwave radiation.

The object of the present invention is also achieved by an apparatus for the measurement of humidity and/or density on a measurement target. The apparatus of the present invention has a microwave sender, a microwave receiver and an analysing unit. The analysing unit can determine the phase and the amplitude for microwave radiation received by the microwave receiver that had been emitted by the microwave sender, the determination taking preferably place in relation to the emitted microwave. Further, the analysing unit can store a complex-valued transfer function of the measurement arrangement. The apparatus of the present invention has an analysing unit which analyses the microwave radiation transmitted through the measurement target, and calculates a complex-valued transmission function of the measurement target taking into account the complex-valued transfer function of the measurement arrangement. The analysing unit has further means for transforming the complex-valued transmission function into the time domain. Let the transformed transmission function be the time domain function. The main pulse of the time domain function is also analysed by the analysing unit. The analysing unit has further means for determining the point in time A for which the main pulse of the time domain function takes on a maximum, and the width B and/or the amplitude value H of the main pulse of the time domain function as characteristic variables for the determination of humidity and/or density. Further provided is a characteristic variable analysing unit which can determine a humidity- and/or density value for the measurement target from the characteristic variable A and at least one of the characteristic variables B and H.

The apparatus of the present invention has an analysing unit which processes the analysed signals at first in the frequency domain in order to determine a complex-valued transmission function for the measurement target. Further, the analysing unit has means for transforming the complex-valued transmission function into a complex-valued time domain function and for determining the characteristic variable A as well as the characteristic variables B and/or H for the occurrence of the main pulse of the complex-valued time domain function. The characteristic variable analysing unit that is provided according to the present invention, which may also be a component of the analysing unit, determines then a humidity- and/or density value for the measurement target from the characteristic variables.

In a preferred embodiment, a conveying device for the measurement target is provided between microwave receiver and microwave sender. The conveying device makes it possible to transport a measurement target that is to be measured continuously through the transmission path between microwave sender and microwave receiver, and to determine humidity- and/or density values for the measurement target continuously and permanently by doing so.

In a preferred embodiment, the apparatus is equipped with at least one temperature measurement device, in order to acquire the temperature of the measurement target, the measurement arrangement and/or a temperature of the surroundings. The temperature acquisition can take place by the temperature measurement device for the three temperature values, or even for less temperature values.

DETAILED DESCRIPTION OF EACH OF THE FIGURES OF THE DRAWINGS

A preferred example of the realisation of the present invention is explained by means of the figures in the following.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
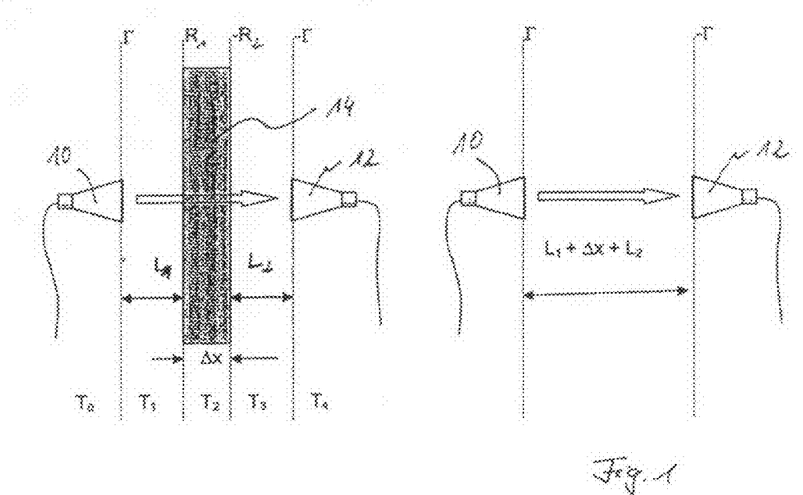
FIG. 1 shows a setup of the transmission path with and without measurement target between sender and receiver.

On the left side, FIG. 1 shows a microwave sender 10 and a microwave receiver 12 directed towards the same, which can receive the emitted microwaves of the microwave sender, A measurement target 14, depicted schematically, is disposed in the transmission path between the microwave sender 10 and the microwave receiver 12. The distance between microwave sender and microwave receiver is composed of the paths $L_1$, $\Delta x$ and $L_2$. The right side part of FIG. 1 shows the setup in which no measurement target is disposed between the microwave sender 10 and the microwave receiver 12. In this, the transmission path has the length $L_1+\Delta x+L_2$.

For a better understanding of the transmission properties of the measurement path of microwave radiation between the microwave sender 10 and the microwave receiver 12, the transmission path can be subdivided by four boundary surfaces with the following reflectivities, as depicted in the left side part of FIG. 1: $\Gamma$, $R_1$, $-R_2$ and $-\Gamma$. In total, five regions result from the boundary surfaces here, to which one of the transfer functions $T_0$, $T_1$, $T_2$, $T_3$ and $T_4$ can be associated at a time. The individual transfer functions are associated to the individual regions of the transmission path on the left side of FIG. 1. The following expression approximatively results for the transfer function T of the complete measurement path when the individual regions are considered:

$$T = T_0 \cdot (1-\Gamma) \cdot e^{-i k_0 \cdot L_1} \cdot (1-R_1) \cdot e^{-i k_0 \cdot (n-i \cdot k) \cdot \Delta x} \cdot (1+R_2) \cdot e^{-i k_0 \cdot L_2} \cdot (1+\Gamma) \cdot T_4$$

In this $\Gamma$, $R_1$, $R_2$ represent the reflectivity at the transitions between the region boundaries, as the same are drawn in at the left side part of FIG. 1, wherein $$k_0 = \frac{2 \cdot \pi \cdot f}{c_0}$$

designates the wavenumber, with the frequency f and the vacuum light velocity $c_0$, the active component n and the reactive component k of the complex refraction coefficient n-ik. $T_0$ and $T_4$ are not further specified transfer functions from the regions before and behind the microwave sender/-receiver 10 and 12, respectively.

Considering the empty measurement arrangement without measurement target in the transmission path with the same approach, the transfer function of the measurement arrangement $T_{empty}$ results approximatively as:

$$T_{empty} = T_0 \cdot (1-\Gamma) \cdot e^{-i k_0 \cdot (L_1+\Delta x+L_2)} \cdot (1-+\Gamma) \cdot T_4$$

By a division of the transfer function T through the transfer function of the measurement arrangement $T_{empty}$ results the following expression, which represents an approximation of the transmission function of the measurement target:

$$\frac{T}{T_{empty}} = (1-R_1) \cdot (1+R_2) \cdot e^{-i k_0 \cdot ((n-1)-i \cdot k) \cdot \Delta x}$$

From the expression it can be recognised clearly that the same still depends on parameters of the measurement target only, that is to say on $R_1$, $R_2$, n, k and $\Delta x$, wherein $\Delta x$ designates the length of the transmitted path in the measurement target, namely its thickness. All the properties that result due to the measurement arrangement do not apply in this point of view in the frequency representation. That is to say, the dependence on the variables $L_1$ and $L_2$ is subtracted out of the transmission function of the measurement target. Further, the reflectivities $\Gamma$ of microwave sender or -receiver do not play any role also. The not further specified transmission functions $T_0$ and $T_4$ are also withdrawn from the expression, so that there is a representation of the transmission function that depends on the measurement target only.

In this, it is dealt with an approach to the transfer conditions in the first order, which can also be continued in the second order. In the second order, that radiation is taken into account, which reciprocates between the measurement target and the aperture surfaces of the antennae and interferes with the remaining radiation. In an approximation of the second order results the following transmission function for the measurement target:

$$\frac{T'}{T_{empty}} = \frac{T}{T_{empty}} \cdot \begin{pmatrix} 1 - \Gamma \cdot R_1 \cdot e^{-2i \cdot k_0 \cdot L_1} - \\ \Gamma \cdot R_2 \cdot e^{-2i \cdot k_0 \cdot L_2} - \\ \Gamma^2 e^{-2i \cdot k_0 \cdot (L_1 + \Delta x + L_2)} \end{pmatrix}$$

wherein the expression $T/T_{empty}$ corresponds to the expression from above. It can be clearly recognised in the expression that there is a dependence on the terms $L_1$, $L_2$ and $\Gamma$. From the consideration in the second order, it becomes already clear that the result has a strong dependence on the wavenumber, that is to say on the frequency and on the distance change within the measurement arrangement. Each one of the additional terms is multiplied by the term $T/T_{empty}$ which is properly intended to be measured, and depends on unknown variables. Thus, these terms cannot be subtracted out without additional presumptions or methods, the last term in particular, which depends only on variables that don't belong to the measurement target. In the state of the art, it has hitherto been attempted to suppress the above disturbing term by averaging over the frequencies and/or distances, or by minimising the reflectivities $\Gamma$, $R_1$ and $R_2$ by different measures. Such methods are described in U.S. Pat. No. 3,079,551, U.S. Pat. No. 3,501,692, U.S. Pat. No. 3,681,684 and U.S. Pat. No. 4,788,853, for instance. The approach of the present invention leaves this consideration of the disturbing term behind and does not attempt to average the same out in the frequency domain or to suppress it otherwise.

In the approach of the present invention, the measured transmission function for the measurement target is transformed into the time domain and analysed further as a function of time.

In the approach of the present invention, the measured transmission function for the measurement target is transformed into the time domain by an inverse Fourier transform. The expression Fourier transform represents that class of linear transformations which convert the time domain representation of a function into its frequency domain representation. For instance, a Fast Fourier transform and/or a sinus-cosinus transform can be used, each of which transforms the more discrete frequency domain representation into the discrete time domain representation.

In order to clarify the result, the function T, divided by $T_{empty}$, will be considered as a complex-valued function $\tau$ in the time domain in the following. The time domain function $\tau$ results in the first order as:

$$\tau_{time\ domain} = inv.F.(T/T_{leer})$$

$$= (1 - R_1)(1 + R_2) \frac{c_0/2\pi}{k \cdot \Delta x - i \cdot (t \cdot c_0 - (n-1) \cdot \Delta x)}$$

Considering the amount of the function $\tau$, the following representation results:

$$|\tau_{time\ domain}| = (1 - R_1)(1 + R_2) \frac{c_0/2\pi}{\sqrt{(k \cdot \Delta x)^2 + (t \cdot c_0 - (n-1) \cdot \Delta x)^2}}$$

By way of the formula, it can be recognised clearly that the time domain function $\tau$ has a maximum, which is reached for the point of time T=A with $$A = \frac{(n-1) \cdot \Delta x}{c_0}$$

It can also be recognised clearly that the point of time A of the maximum of the time domain function depends only on the material variables n and $\Delta x$.

The maximum value of the amplitude H in the time domain function results as:

$$H = \frac{c_0}{2\pi \cdot k \cdot \Delta x}$$

It can be recognised clearly that again, the variable H depends only on the reactive component of the refractive index k and the thickness of the measurement target $\Delta x$.

The product of the reactive component of the complex-valued refractive index k and the thickness $\Delta x$ of the measurement target can also be determined from the half-band width of the main pulse of the time domain function. Starting from the time domain function, the half-band width of a main pulse results as $$B = 2 \cdot \sqrt{3} \cdot k \cdot \Delta x$$

Thus, the variable B can be determined either from the half-band width of the main pulse, or be calculated from the characteristic variable H:

$$B = \frac{c_0}{H} \cdot \frac{\sqrt{3}}{\pi}$$

Figure 2:
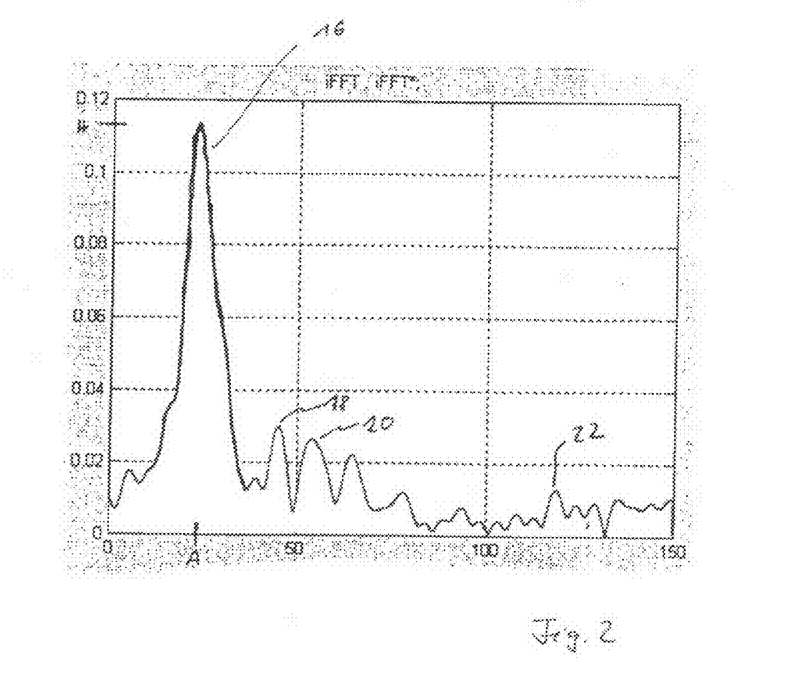
FIG. 2 shows the absolute amount of the complex-valued time domain function.

FIG. 2 shows the amount of the time domain function as the same occurs in a measurement. It can be recognised clearly that a sharp clear peak 16 emerges after the transformation into the time domain. By this peak, the characteristic variables A and H and/or B can be determined.

Taking into account now in the second order the already mentioned disturbances which arise through reflections in the measurement path and which strongly depend on the variables $L_1$, $L_2$ and $\Delta x$, the same are subtracted out in the consideration of the complex-valued time domain function, because they later appear as the main pulse 16. For the rest, the distances occur with smaller amplitude values than the main signal which is reflected in the main pulse, because they are based on disturbances of the second order and thus they depend on the product of two reflectivities.

For instance in FIG. 2, the disturbing signals that depend on $L_1$ can be identified with 18, those depending on $L_2$ with 20 and those disturbing signals that are based on $L_1 + L_2 + \Delta x$ with 22.

In a consideration of the transmission functions of the measurement target in the frequency domain, a reliable separation of measurement signal and disturbing signal is very difficult, and it necessitates a sumptuous numerical treatment of the disturbance terms. By the transformation into the time domain, helpful signals 16 and the disturbing signals 18, 20 and 22 that superimpose the same are separated from each other due to the different runtime.

In the invention, an analysis of the main helpful signal takes then place in its main pulse 16, wherein the point in time A of the occurrence of the maximum value of the main pulse yields a first characteristic variable for the determination of humidity and/or density, because it is proportional to the active component of the refractive index n reduced by 1 and the thickness $\Delta x$ of the measurement target. The height of the main pulse is inversely proportional to the reactive component k of the refractive coefficient and to the thickness $\Delta x$ of the measurement target.

Due to the limited frequency band in the measurement, the main pulse experiences a certain deviation in its height H and its width B with respect to a pulse that would result with an infinite frequency band. The point in time A at which the main pulse occurs is not changed by the finite frequency range. If one considers a transformation from the frequency domain into the time domain in a finite frequency interval from $f_{Start}$ up to $F_{stop}$, approximatively the following expression results using $F_{Center} = \frac{1}{2}(f_{Start} + f_{Stop})$:

$$B = \frac{1 - \frac{H}{H_0}}{2 \cdot \pi \cdot f_{Center}} \text{ with } f_{Center} = \frac{f_{Start} + f_{Stop}}{2}$$

$H_0$ is a product-specific constant, which is determined only once for the product that is to be measured.

Figure 3:
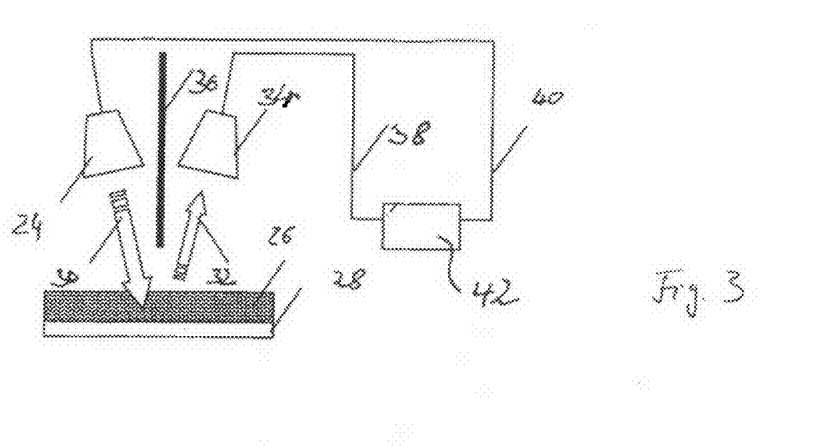
FIG. 3 shows the setup for a transmission measurement using a reflecting plate.

FIG. 3 shows the schematic setup in a transmission measurement using a reflector. A microwave sender 24 is directed to the measurement target 26 that is disposed on a reflector 28. The microwave radiation 30 emitted by the microwave sender 24 passing through the measurement target 26 hits the reflector 28, and after passage through the measurement target 26 anew, it is received by the microwave receiver 34 as reflected radiation 32. In order to prevent direct cross-talk between microwave sender 24 and microwave receiver 34, the same are shielded from each other through a separation wall 36. Microwave sender 24 and microwave receiver 34 guide their signals to a network analyser 42 via a cable 38 and a cable 40, respectively. The network analyser 42 determines then the attenuation of the emitted microwave radiation 30 by the measurement target 26. The network analyser determines also the phase shift of the microwave signal 30 due to the twofold passage through the measurement target 26, and as the case may be due to the reflection on the reflector 28.

Figure 4:
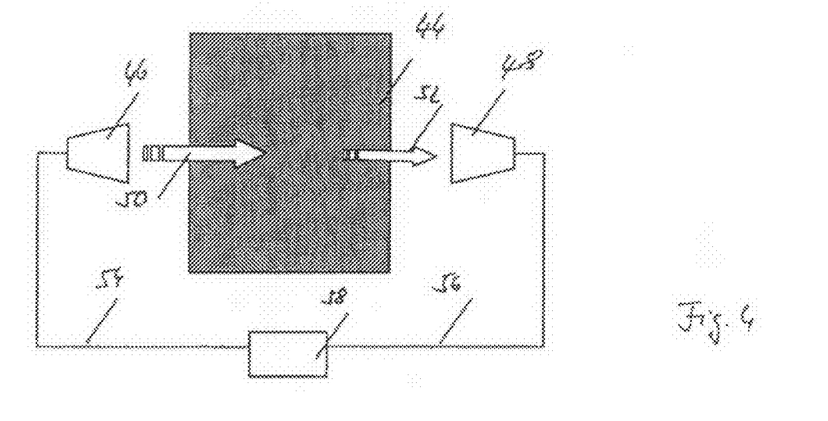
FIG. 4 shows the setup of the measurement arrangement with opposing microwave sender and -receiver.

FIG. 4 shows an alternative setup, wherein the measurement target 44 is located between the microwave sender 46 and the microwave receiver 48. The microwave radiation 50 emitted by the microwave sender 46 is transmitted through the measurement target 44 under alteration of phase and amplitude, and hits the microwave receiver 48. In order to analyse the attenuation and the phase shift, microwave sender and microwave receiver are connected to a network analyser 58 via two cables 54 and 56.

Figure 5:
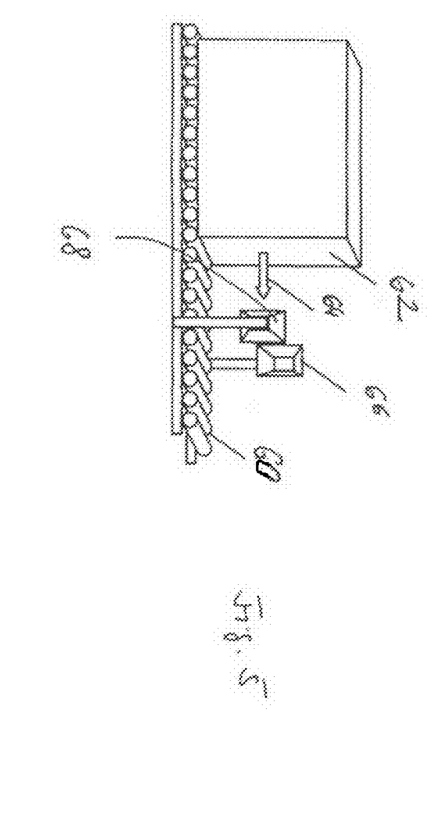
FIG. 5 shows a three-dimensional representation of the setup according to FIG. 4.

FIG. 5 shows a cut-out of a preferred embodiment of the measurement setup. Along a conveying path 60, the measurement target 62 is moved in the direction 64 between microwave sender 60 and microwave receiver 68. The associated analysing unit is not depicted in FIG. 5.

Thus, a density-independent humidity value and/or a humidity-independent density value is/are determined starting from the characteristic variables A and B. In the following, the determination of the density-independent humidity value will be explained first:

The analysis of the characteristic variables for the determination of the humidity in the product takes place by a method that is per se known, as the same is for instance used in the resonator technique also.

Figure 7:
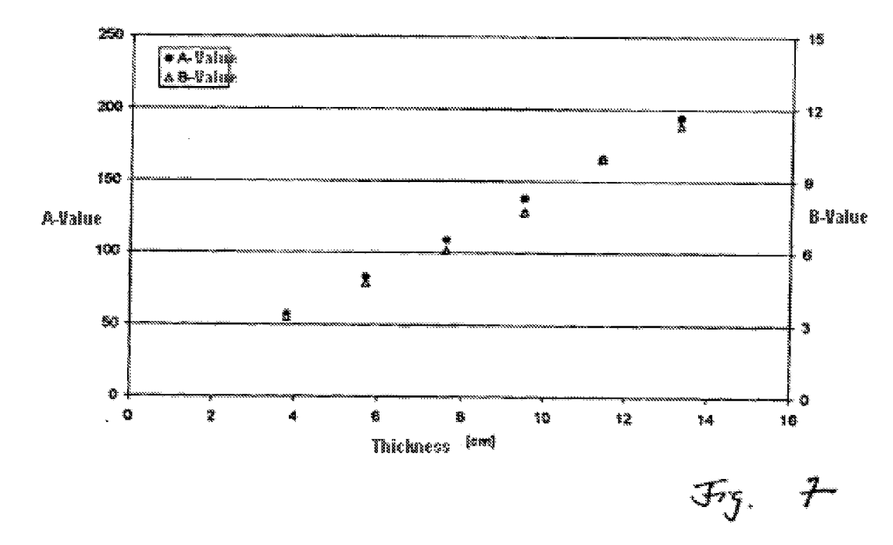
FIG. 7 shows the dependence of the characteristic variables A and B on the thickness in press boards.

For the calibration, samples having different humidities are measured with the method of the present invention, and the characteristic variables A and B are determined at known humidity of the product. When the characteristic variable B is mentioned in the following, the characteristic variable H can always be used also, provided that the same had been correspondingly converted into the characteristic variable B. The humidity value $$\phi = \frac{B}{A}$$

is compared for the measured characteristic variables with the corresponding humidity of the product which had been determined with the aid of a reference method. One recognises clearly in FIG. 7 that the A-value and the B-value is always proportional to the thickness of the measurement target at a time. Thus, the humidity value $\phi$ as defined above is independent of the thickness of the measurement target. Further measurements have shown that analogous relations hold also with respect to the density of the measurement target. Thus, the humidity value $\phi$ is independent of the density and the thickness of the measurement target.

A calibration relation is determined by a curve fit, and stored for instance in the analysing unit. In general, this calibration relation may have the following form:

humidity=$f(\phi)$ wherein f is a product-independent, at least in parts continuous function. In the simplest case, there is a linear relation between the humidity and the humidity value $\phi$:

humidity=$\alpha \cdot \phi + \beta$ wherein the real-valued calibration parameters $\alpha$ and $\beta$ can be determined by linear regression of the humidity values and the reference humidity values, for instance.

Figure 6:
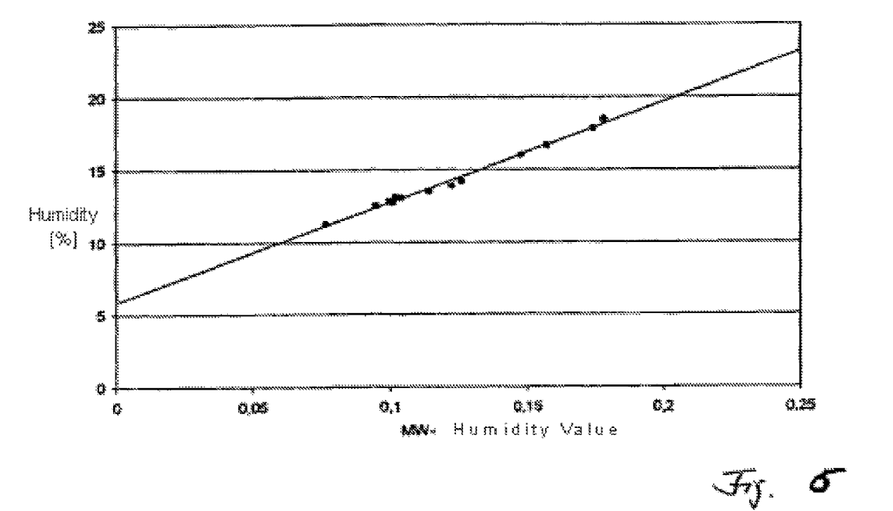
FIG. 6 shows the dependence of the humidity on a measured humidity value in a tobacco bale.

FIG. 6 shows such a linear regression of the measured humidity values $\phi$, designated as MW-humidity values, with respect to the reference humidity. It can be clearly recognised that there is a linear interrelationship with the reference humidity over a wide range of the MW-humidity values.

The density by surface g can also be determined in a further calibration phase. The density by surface g is defined as the mass of the measurement target, related to a unit area of a plane which stands vertical to the propagation direction of the microwave. The density by surface is compared with the measured humidity value $\phi$, the corresponding A-values and the corresponding B-values. A calibration relation for the density by surface is determined by a curve fit. This calibration relation for the density by surface has generally the following form:

density by surface=$g(A,B,\phi)$ wherein g is a product-dependent, but humidity-independent function. Comparison measurements have shown that in the simplest case, there is the following interrelation between the density by surface, the humidity value ϕ and the A-value:

$$\text{density by surface} = \gamma \cdot \phi \cdot A + \delta \cdot A + \in$$

wherein the real-valued calibration parameters $\gamma$, $\delta$, $\in$ can be obtained for instance by linear regression of the humidity values ϕ and the A-values on the reference densities by surface.

In FIG. 7, the A- and the B-values for one humidity are plotted against the thickness. It can be clearly recognised that there is a linear interrelationship with the thickness of the measurement target in both cases, so that the density by surface can be calculated from this.

When the spatial extension of the measurement target in the propagation direction is known, for instance because it is set as constant or because it is measured by an independent method in addition, then the average density of the entire measurement target can be determined from the measured density by surface. In particular, the active component n as well as the reactive component k of the complex refraction coefficient can then be determined from the A- and the B-value. When the density of the measurement target is known, the thickness of the measurement target can also be determined from the measured density by surface.

The measured characteristic variables A, B and H are in general temperature dependent. Different comparative investigations have shown that the dependence on different temperatures $T_{e1}$, $T_{e2}$, $T_{e3}$ ... can be linearly approximated. For instance, the humidity can be represented as depending on temperature as:

$$\text{humidity} = \left(\alpha_0 + \sum_i \alpha_i \cdot Te_i\right) \cdot \phi + \beta_0 + \sum_i \beta_i \cdot Te_i$$

wherein $\alpha_i$, $\beta_i$ are temperature-independent real-valued coefficients and $\{Te_i\}$ designates different temperatures.

In analogy to the approach for the humidity determination, the temperature dependence of the density by surface can be determined as follows:

density by surface =

$$\left(\lambda_0 + \sum_i \lambda_i \cdot Te_i\right) \cdot \phi \cdot A + \left(\delta_0 + \sum_i \delta_i \cdot Te_i\right) \cdot A + \varepsilon_0 + \sum_i \varepsilon_i \cdot Te_i$$

wherein the coefficients $\{\lambda_i, \delta_i, \in_i\}$ are temperature-independent coefficients. As different temperatures can be acquired, for instance, the temperature of the measurement target, the surroundings temperature or the temperature of the measurement device.

Experiments on measurement targets of layered nature have shown that the measurement values A and B are independent of the spatial orientation of the material layers when circularly polarised electromagnetic radiation is used, provided that the microwave radiation hits the layers at a slant angle. Layered measurement targets can be measured independent of their orientation when circularly polarised electromagnetic radiation is used.

When linearly polarised electromagnetic radiation is used, density-independent humidity values or humidity-independent values for the density by surface can be obtained for layered measurement targets, when in a second measurement operation, the direction of the polarisation of the microwave radiation is rotated about 90° with respect to the direction in the first measurement operation, or when the propagation direction of the microwave stands vertical on the material layers.

Alternatively, the measurement operation can be repeated several times with different polarisation directions, wherein the direction of the polarisation of the electromagnetic radiation is always changed about a certain angle with respect to the previous measurement operation. That polarisation angle at which the B-value has its minimum value or alternatively, its maximum value, can be determined by interpolation from the so determined characteristic variables which depend on the polarisation direction. The measurement can be repeated for this polarisation angle, and the correspondingly obtained characteristic variables can be analysed as described above.

For a spatially extended measurement target, like a cardboard box or a bale e.g., a humidity value or an average value for the density by surface or the density of the measurement target can be measured along the profile of the measurement target. For this purpose, the measurement target is advanced through the measurement path, or the measurement setup with microwave sender and -receiver is moved along the measurement target.

The measurement method of the present invention is distinguished with respect to known transmission methods by a number of features. At first, it is a two parameter method, wherein two characteristic variables A and B are determined for further analysis. Weighing the product or measuring the thickness of the measurement target can be omitted in this. The method of the present invention is particularly suited for contact-free density- and thickness-independent humidity measurement. An important aspect in this is to perform the measurement in the frequency domain, and to change over into the time domain after a first analysis in the frequency domain, that is to say after a division of the obtained complex-valued transfer function through the transfer function of the measurement arrangement, in order to determine the complex-valued transmission function for the measurement target. The measurement in the frequency domain has the advantage that the effect of the empty antenna path is eliminated from the measurement data by the division through the complex-valued transfer function of the measurement setup. Thus, the transmission function of the measurement target determined in this way is independent of the transfer function of the antenna path, thus independent of the utilised antennae, the cable lengths, the distances of the antennae from the measurement target and the like. By the transformation of the measured transmission function of the measurement target into the time domain, the wave proportions that are reflected on jump layers of the refraction coefficient, for instance on the measurement target or on the aperture surfaces of the antenna, and therefore have a longer running path than the helpful signal, can be separated from the helpful signal. In the time domain representation, these signals are following on the maximum value and have very small amplitudes in the region of the main pulse. Therefore, the position of the measurement target within the antenna path and the exact orientation thereof has only a small influence on the measurement results.

Thus, the analysis of the main pulse of the time domain function makes sure that reflections and superimpositions are removed from the signals. By the combination of the approaches in the frequency- and in the time domain according to the present invention, very accurate characteristic variables can be found for a density-independent humidity determination and a humidity-independent density determination. The determination of the measurement variable B from the measurement variable H in dependence on the starting- and the stop frequency provides that the B-value is proportional to the thickness Δx and to the reactive component k of the complex refraction coefficient of the measurement target in a very good approximation.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for the measurement of humidity or density in a measurement target, with a microwave sender, a microwave receiver and an analysing unit, which can determine the phase and the amplitude for microwave radiation of the microwave sender received by the microwave receiver, and in which a complex-valued transfer function of the measurement arrangement can be stored, the method having the following steps:
    determining the phase and the amplitude of the microwave radiation transmitted through the measurement target for a number of frequencies in one measurement operation;
    calculating the complex-valued transmission function of the measurement target from the determined values using the complex-valued transfer function of the measurement arrangement;
    transforming the complex-valued transmission function of the measurement target into the time domain as a complex-valued time domain function;
    determining the point in time at which the amount of the main pulse has its maximum value as a first characteristic variable from the time domain function;
        determining a second characteristic variable wherein said second characteristic variable is selected from the following values: the width of the main pulse, the amplitude value of the main pulse and combinations of these values, and
        determining a density-independent humidity or a density of the measurement target depending on the first characteristic variable and the second characteristic variable.

2. A method according to claim 1, wherein in a measurement operation without measurement target between microwave sender and microwave receiver, the phase and the amplitude of the microwave radiation emitted by the microwave sender is determined for a number of frequencies, and the complex-valued transfer function of the measurement arrangement is determined from this, which is saved in the analysing unit.

3. A method according to claim 1, wherein the amount of the complex-valued time domain function is analysed in order to determine the characteristic variables.

4. A method according to claim 1, wherein the active component and/or the reactive component of the complex-valued time domain function is analysed in order to determine the characteristic variables.

5. A method according to claim 1, wherein in the measurement operation, the frequencies come from a frequency interval with a smallest frequency $f_{Start}$ and a greatest frequency $f_{Stop}$.

6. A method according to claim 5, wherein the start frequency is 500 kHz and the stop frequency is 50 GHz, preferably the start frequency is 500 MHz and the stop frequency is 20 GHz.

7. A method according to claim 5, wherein the second characteristic variable is calculated depending on the amplitude value, taking into account the lowest frequency $f_{Start}$ and the greatest frequency $f_{Stop}$ of the frequency interval.

8. A method according to claim 1, wherein the second characteristic variable is determined as the reciprocal value of the amplitude value of the main pulse.

9. A method according to claim 1, wherein the humidity of the measurement target is determined depending on the humidity value φ, which depends on at least two of the characteristic variables.

10. A method according to claim 9, wherein the humidity value φ is the quotient of the second and first characteristic variables.

11. A method according to claim 9, wherein the humidity value φ is the arc tan of the quotient of the first and second characteristic variables.

12. A method according to claim 9, wherein a density by surface g of the measurement target is determined depending on the humidity value φ, and at least one of the first and second characteristic variables.

13. A method according to claim 9, wherein a density of the measurement target is determined in addition, depending on the humidity value φ, the thickness of the measurement target and at least one of the first and second characteristic variables.

14. A method according to claim 1, wherein the determination of at least one of the following values: humidity, density by surface or density, takes place depending on at least one measured temperature.

15. A method according to claim 14, wherein the temperature of the measurement target is measured.

16. A method according to claim 14, wherein a temperature of the measurement arrangement is measured in addition or solely.

17. A method according to claim 14, characterised in that a temperature of the surroundings is measured in addition or solely.

18. A method according to claim 1, wherein the emitted microwave radiation is polarized.

19. A method according to claim 18, wherein the microwave radiation is circularly polarized.

20. A method according to claim 18, wherein the measurement operation is performed with linearly polarized microwave radiation.

21. A method according to claim 20, wherein the measurement operation is repeated plural times for each measurement target with different polarization directions, the polarization direction being changed in every repetition.

22. A method according to claim 21, wherein the determination of the first and second characteristic variables takes place at a polarization angle at which the second characteristic variable B has a minimum value.

23. A method according to claim 1, wherein the measurement target is moved between microwave sender and microwave receiver.

24. The method of claim 1 wherein both the density-independent humidity and the density of the measurement target are determined.

25. An apparatus for the measurement of humidity and/or density in a measurement target, comprising:
a microwave sender;
a microwave receiver; and
an analysing unit, that determines the phase and the amplitude for microwave radiation emitted by the microwave sender for the microwave receiver and stores a complex-valued transfer function of the measurement arrangement;
wherein the analysing unit analyses the microwave radiation transmitted by the measurement target and determines a complex-valued transmission function of the measurement target taking into account the complex-valued transfer function of the measurement arrangement;
the analysing unit has further means for transforming the complex-valued transfer function into the time domain as a time domain function, and to analyse the main pulse of the time domain function;
the analysing unit has further means for determining a point in time A for the main pulse of the time domain function as a characteristic variable, and the width B and/or the amplitude value H of the main pulse of the time domain function as additional characteristic variable, and has a characteristic variable analysing unit for humidity and/or density, which can determine a density-independent humidity value and/or a density value for the measurement target from the characteristic variable A and at least one of the characteristic variables B and H.

26. An apparatus according to claim 25, wherein at least one temperature measurement device is provided in order to acquire the temperature of the measurement target, the measurement arrangement and/or of the surroundings.

27. An apparatus according to claim 25, wherein a conveying device for the measurement target is provided between microwave receiver and microwave sender.

28. A method for the measurement of humidity or density in a measurement target, with a microwave sender, a microwave receiver and an analysing unit, which can determine the phase and the amplitude for microwave radiation of the microwave sender received by the microwave receiver, and in which a complex-valued transfer function of the measurement arrangement can be stored, the method having the following steps:
determining the phase and the amplitude of the microwave radiation transmitted through the measurement target for a number of frequencies in one measurement operation;
calculating the complex-valued transmission function of the measurement target from the determined values using the complex-valued transfer function of the measurement arrangement;
transforming the complex-valued transmission function of the measurement target into the time domain as a complex-valued time domain function;
determining the point in time at which the amount of the main pulse has its maximum value as a first characteristic variable A from the time domain function;
determining a second characteristic variable, wherein said second characteristic variable is selected from the following values: the width of the main pulse, the amplitude value of the main pulse and combinations of these values, and
determining a density of the measurement target depending or a density-independent humidity on the first characteristic variable and the second characteristic variables.

* * * * *

UNITED STATES PATENT AND TRADEMARK OFFICE
CERTIFICATE OF CORRECTION

| | | |
|---|---|---|
| PATENT NO. | : 8,354,849 B2 | Page 1 of 1 |
| APPLICATION NO. | : 12/740724 | |
| DATED | : January 15, 2013 | |
| INVENTOR(S) | : Hendrik Richter | |

It is certified that error appears in the above-identified patent and that said Letters Patent is hereby corrected as shown below:

In the Claims:

Column 17, line 11, delete "B".

Signed and Sealed this
Seventh Day of May, 2013

Teresa Stanek Rea
*Acting Director of the United States Patent and Trademark Office*